US00PP22322P3

(12) United States Plant Patent
Karniel et al.

(10) Patent No.: US PP22,322 P3
(45) Date of Patent: Dec. 13, 2011

(54) GRAPE PLANT NAMED 'ARRAELEVEN'

(50) Latin Name: *Vitis vinifera*
Varietal Denomination: ARRAELEVEN

(75) Inventors: Shachar Karniel, Edison, CA (US); Sal Giumarra, Edison, CA (US)

(73) Assignee: Agricultural Research and Development Limited Liability Company, Edison, CA (US)

( * ) Notice: Subject to any disclaimer, the term of this patent is extended or adjusted under 35 U.S.C. 154(b) by 0 days.

(21) Appl. No.: 12/660,726

(22) Filed: Mar. 2, 2010

(65) Prior Publication Data

US 2011/0219503 P1 Sep. 8, 2011

(51) Int. Cl.
*A01H 5/00* (2006.01)

(52) U.S. Cl. ..... Plt./207

(58) Field of Classification Search ..... Plt./205, Plt./207
See application file for complete search history.

(56) References Cited

U.S. PATENT DOCUMENTS

PP16,399 P3 4/2006 Ellis et al.
PP17,223 P3 11/2006 Giumarra et al.
PP17,224 P3 11/2006 Giumarra et al.
PP18,625 P3 3/2008 Pinhas et al.

*Primary Examiner* — Susan McCormick Ewoldt
(74) *Attorney, Agent, or Firm* — Christie, Parker & Hale, LLP

(57) ABSTRACT

A new distinct variety of grapevine named ARRAELEVEN abundantly forms attractive medium-to-large seedless berries having green / creamy yellow skin coloration in medium-to-large clusters. The fruit displays a sweet Muscat flavor and is firm in texture. The fruit commonly is ready for harvesting during the end of July in San Joaquin Valley of Central California, U.S.A, and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has the varietal denomination 'ARRAELEVEN'.

BACKGROUND OF THE INVENTION

A breeding program was initiated during the late 80's near Bakersfield in San Joaquin Valley of Central California. In 1989, during this breeding program, a new variety of *Vitis vinifera* was created by deliberate cross breeding of two parent plants by emasculation of the pollen bearing organ of the male and introducing pollen from another male origin. The female parent of the new variety was the GAW2 which is a light green, obtuse ovoid shaped grape variety bearing a very small remainder of seed rudiment (non-patented in the United States). The male parent (i.e. the pollen parent) of the new variety was GRAPAES (U.S. Plant Pat. No. 12,696) which is an oval shaped, creamy green colored, seedless variety with a Muscat flavor.

Comparison between ARRAELEVEN and Thompson Seedless

| | ARRAELEVEN | Thompson Seedless |
|---|---|---|
| Pruning | Spur pruning | Cane pruning |
| Leaf color | Top side: yellow-green (146 A) Bottom side: yellow-green (146 B) | Top side: yellow-green (137 A) Bottom side: yellow-green (137 C) |
| Berry shape | Ovoid | Cylindrical |

The parentage of the new variety can be summarized as follows:

GAW2×GRAPAES

An artificial pollination was created, and the result was an embryo which possessed unique genetic qualities. The rudiments resulting from the above pollination were embryo rescued.

In 2000 the plant was then transplanted to Bakersfield in San Joaquin Valley of Central California.

It was found that the new grapevine of the present invention possesses the following combination of characteristics:

(a) Forms attractive medium-to-large seedless berries having green/ creamy yellow skin coloration in medium-to-large clusters which display a very sweet Muscat flavor;
(b) Commonly bears fruit during the end of July in the San Joaquin Valley of Central California, U.S.A.; and
(c) Bears fruit that is firm and is well amenable for storage, handling, and shipping.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2003 near Bakersfield in the San Joaquin Valley of Central California, U.S.A. by grafting on mature 'Thompson Seedless' rootstock (non-patented in the United States). Such asexual propagation has been conducted thereafter in successive years through 2006, and has shown that the characteristics of the new variety are strictly transmissible from one generation to another. Accordingly, the new variety undergoes asexual propagation in a true to type manner. The age of the plant in the drawing is five years old and the variety was created in 1989.

SUMMARY OF INVENTION

The new variety ARRAELEVEN is a elongated, green/creamy yellow seedless table grape with large production, e.g., about 40 to 50 bunches per vine, and an average of about one to two bunches per shoot.

Asexual reproduction by micro propagation of the new variety as performed near Bakersfield, Calif., U.S.A., at Arvin, Calif. Ranch 33 which shows that the forgoing and other distinguishing characteristics come true to form and are established and transmitted through succeeding propagations.

Dimensions in centimeters are shown at the top of the photograph for comparative purposes.

BRIEF DESCRIPTION OF THE DRAWINGS

The accompanying photographic illustration shows typical specimens of vegetative growth of five year old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRAELEVEN'.

DETAILED BOTANICAL DESCRIPTION

The chart used in the identification of colors is The R.H.S. Colour Chart of The ROYAL HORTICULTURAL SOCIETY. The description is based on the observation of plants growing on 'Thompson Seedless' rootstock outdoors near San Joaquin Valley of Central California, U.S.A.

Vine:
- *Vigor.*—Weak vine with thick tendrils and canes. Matures before the harvest.
- *Productive capacity.*—An average of 20-25 tons per hectare.
- *Trunk.*—Strong and developed for its age. Ranges from 2"-2⅜". Surface has a rough surface with a fibrous, shaggy exterior. Coloration is greyed-orange (177-D).

Time of bud burst:
- *Early.*—Date of bud burst in specified location of culture is Mar. 7, 2011 season in Arvin, Calif.

Young shoot:
- *Openness of tip.*—Closed.
- *Prostrate hairs on tip.*—Medium.
- *Anthocyanin coloration of prostrate hairs on tip.*—Weak.
- *Erect hairs on tip.*—Sparse.
- *Color.*—Yellow-green (144-C).

Young leaf:
- *Color of upper side of blade.*—Yellow green; top (yellow green 146-A); bottom (yellow green 146-B).
- *Prostrate hairs between main veins on lower side of blade.*—Sparse.
- *Erect hairs on main veins on lower side of blade.*—Sparse.

Shoot:
- *Attitude (before tying).*—Semi-erect.
- *Color of dorsal side of internodes.*—Green and red (green 143-A; grayed orange 177-A).
- *Color of ventral side of internodes.*—Green (green 143-A).
- *Color of dorsal side of nodes.*—Yellow-green (144-A).
- *Color of ventral side of nodes.*—Yellow-green (144-B).
- *Erect hairs on internodes.*—Absent or very sparse.
- *Length of tendrils.*—3 tendrils 10 cm, 7.5 cm, 6.5 cm.
- *Color of tendrils.*—Yellow-green (145-A).

Flower:
- *Sexual organs.*—Fully developed stamens and fully developed gynoecium Mature leaf:
- *Size of blade.*—Medium (4.5×6.5).
- *Shape of blade.*—Circular.
- *Blistering of upper side of blade.*—Absent or very weak.
- *Number of lobes.*—Five.
- *Depth of upper lateral sinuses.*—Shallow.

Lobed leaves:
- *Arrangement of lobes of upper lateral sinuses.*—Open.
- *Arrangement of lobes of petiole sinus.*—Slightly open.
- *Length of teeth.*—Medium, 3 cm.
- *Ratio length/width of teeth.*—Medium.
- *Shape of teeth.*—Both sides convex.
- *Proportion of main veins on upper side of blade with anthocyanin coloration.*—Low, 3 cm.
- *Prostrate hairs between main veins on lower side of blade.*—Sparse.
- *Erect hairs on main veins on lower side of blade.*—Sparse.
- *Length of petiole equal compared to length of middle vein.*—Moderately shorter, petiole length is 12.5 cm and vein length is 13.5 cm.
- *Top side color.*—Green (138-A).
- *Bottom side color.*—Yellow-green (144-A).
- *Texture.*—Smooth.
- *Petiole length.*—12.5 cm.
- *Petiole color.*—Yellow-green (144-B).
- *Petiole strips color.*—Grayed purple (183-D).
- *Vein color.*—Yellow-green (145-A).

Reproductive organs:
- *Color.*—Green (138-A).
- *Size.*—2 mm.

Time of beginning of ripening: Medium, July 6 Arvin, Calif. season

Bunch:
- *Size (peduncle excluded).*—Medium (6.5"33 5.5").
- *Weight.*—750g.
- *Density.*—Dense, compact.
- *Length of peduncle primary bunch.*—Medium (2").

Berry:
- *Size.*—Large, 22.2 cm.
- *Weight.*—13g.
- *Shape.*—Ovoid.
- *Length.*—3 cm.
- *Color of skin (without bloom).*—Yellow green (yellow green 150-B).
- *Ease of detachment from pedicel.*—Moderately easy.
- *Thickness of skin.*—Medium.
- *Anthocyanin coloration of flesh.*—Medium.
- *Firmness and color of flesh.*—Moderately firm, yellow-green (150-B).
- *Particular flavor.*—None.

*Formation of seeds.*—Rudimentary.

*Berries per bunch.*—70 berries.

*Market use of the observed plant.*—Fresh market.

Woody shoot:

*Main Color.*—Orange brown (grayed orange 164-C).

DNA PROFILE

To further the characterize the new Arra variety DNA was extracted from dried leaf samples and DNA profiles were obtained in Spain, using base pairs for 14 standard microsatellite DNA markers. The data is presented hereafter.

| Microsatellite DNA Marker | Allele Sizes in Base Pairs | |
|---|---|---|
| MSV01 | 134 | 136 |
| MSV02 | 226 | 236 |
| MSV04 | 179 | 193 |
| MSV06 | 250 | 254 |
| MSV07 | 318 | 322 |
| MSV08 | 245 | 268 |

-continued

| Microsatellite DNA Marker | Allele Sizes in Base Pairs | |
|---|---|---|
| MSV09 | 241 | 257 |
| MSV10 | 211 | 211 |
| MSV12 | 256 | 269 |
| MSV13 | 168 | 168 |
| MSV14 | 150 | 158 |
| MSV15 | 295 | 299 |
| MSV16 | 176 | 186 |
| MSV17 | 153 | 159 |

The ARRAELEVEN variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of grapevine, botanically known as *Vitis vinifera*, identified as 'ARRAELEVEN', substantially as shown and described herein.

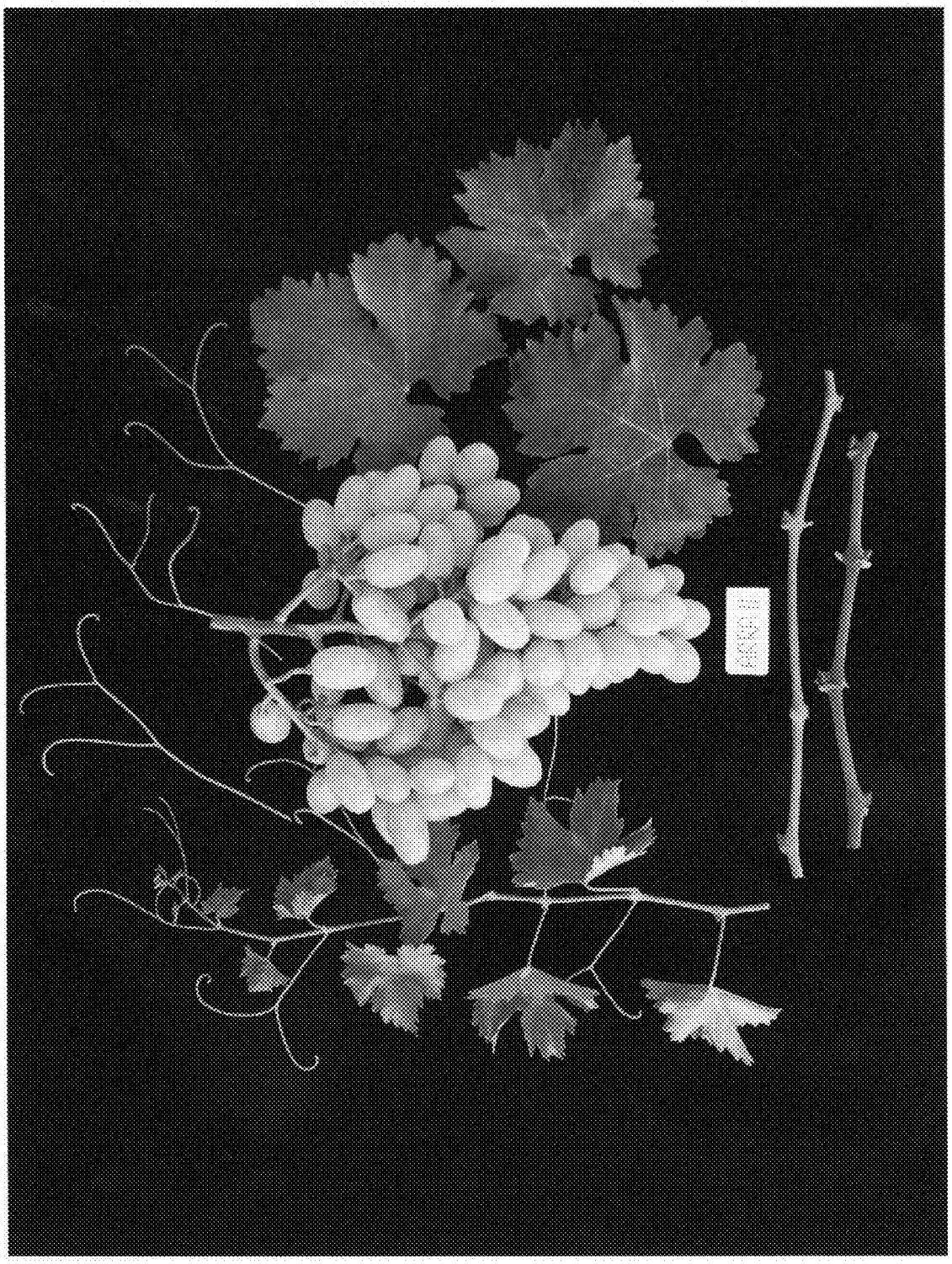

* * * * *